(12) United States Patent
Sevenster

(10) Patent No.: US 11,189,026 B2
(45) Date of Patent: Nov. 30, 2021

(54) INTELLIGENT ORGANIZATION OF MEDICAL STUDY TIMELINE BY ORDER CODES

(71) Applicant: KONINKLIJKE PHILIPS N.V., Eindhoven (NL)

(72) Inventor: Merlijn Sevenster, Haarlem (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 96 days.

(21) Appl. No.: 16/604,306

(22) PCT Filed: Apr. 17, 2018

(86) PCT No.: PCT/EP2018/059734
§ 371 (c)(1),
(2) Date: Oct. 10, 2019

(87) PCT Pub. No.: WO2018/192906
PCT Pub. Date: Oct. 25, 2018

(65) Prior Publication Data
US 2020/0043165 A1 Feb. 6, 2020

Related U.S. Application Data

(60) Provisional application No. 62/486,486, filed on Apr. 18, 2017.

(51) Int. Cl.
*G06T 7/00* (2017.01)
*A61B 34/10* (2016.01)
(Continued)

(52) U.S. Cl.
CPC ............ *G06T 7/0012* (2013.01); *A61B 34/10* (2016.02); *A61K 49/0419* (2013.01);
(Continued)

(58) Field of Classification Search
CPC .............. A61B 2034/101; A61B 34/10; A61K 49/0419; G16H 30/40; G16H 30/20; G06T 7/0012
See application file for complete search history.

(56) References Cited

U.S. PATENT DOCUMENTS

2006/0277073 A1* 12/2006 Heilbrunn .............. G16H 15/00
705/3
2012/0130734 A1* 5/2012 White .................... G16H 30/20
705/2

(Continued)

OTHER PUBLICATIONS

International Search Report and Written Opinion dated Jul. 3, 2018 for International Application No. PGT/EP2018/059734 Filed Apr. 17, 2018.

*Primary Examiner* — Mia M Thomas

(57) ABSTRACT

A radiology viewer includes an electronic processor (10, 22), a display (12), input device(s) (14, 16), and a non-transitory storage medium storing executable instructions. Retrieval instructions (42) are executable to retrieve an index of prior radiology examinations (24, 26) from an electronic patient chart (20) in which the prior radiology examinations are indexed by at least date, imaging modality, and anatomical region and to retrieve billable order codes for the prior radiology examinations from an order management system (30). Organizing instructions (44) are executable to organize the prior radiology examinations into groups using features of the prior radiology examinations including features comprising or generated from the billable order codes for the prior radiology examinations. Viewer instructions (50) are executable to display an organized index of the prior radiology examinations on the at least one display in which the prior radiology examinations are organized into the groups.

18 Claims, 4 Drawing Sheets

Figure 1:
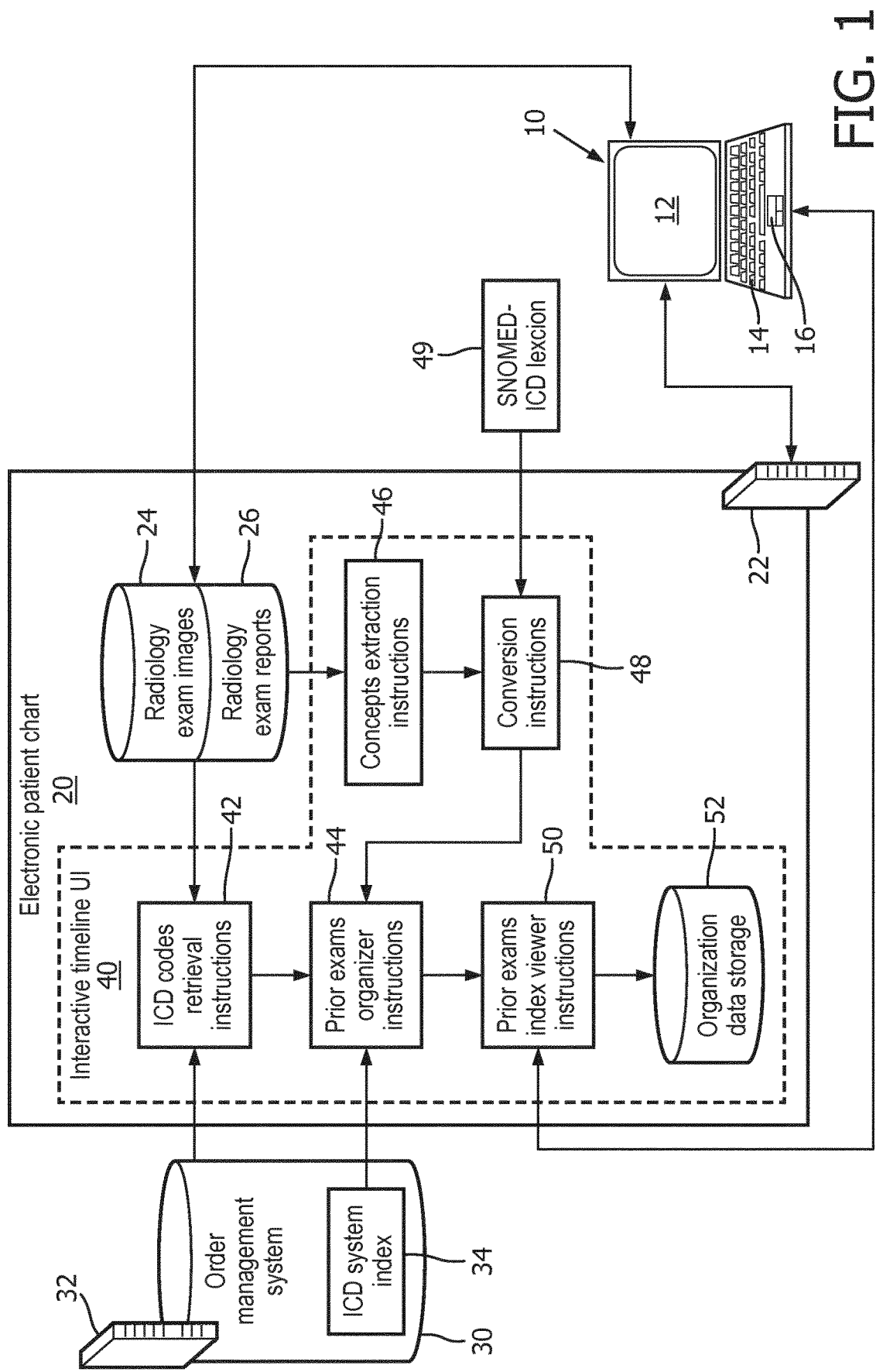

(51) Int. Cl.
   *G16H 30/20* (2018.01)
   *G16H 30/40* (2018.01)
   *A61K 49/04* (2006.01)

(52) U.S. Cl.
   CPC .............. *G16H 30/20* (2018.01); *G16H 30/40* (2018.01); *A61B 2034/101* (2016.02)

(56) References Cited

U.S. PATENT DOCUMENTS

| | | | | |
|---|---|---|---|---|
| 2012/0232927 | A1* | 9/2012 | Larruga | G06Q 10/10 |
| | | | | 705/3 |
| 2016/0210441 | A1* | 7/2016 | Schulze | G06F 40/134 |
| 2018/0233224 | A1* | 8/2018 | Trovato | G16H 30/20 |
| 2018/0286504 | A1* | 10/2018 | Trovato | G16H 15/00 |
| 2020/0176107 | A1* | 6/2020 | Sevenster | G16H 70/20 |
| 2020/0294655 | A1* | 9/2020 | Tahmasebi Maraghoosh | |
| | | | | G16H 10/60 |

\* cited by examiner

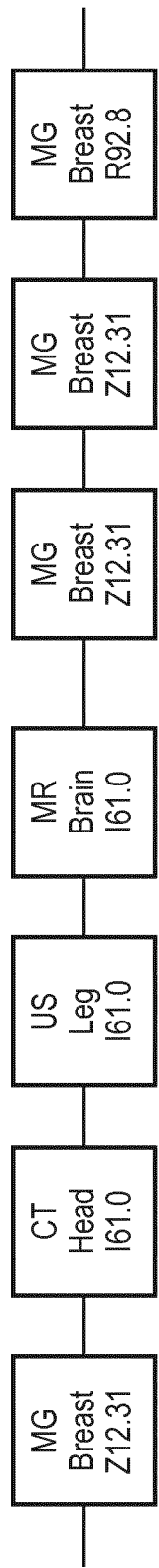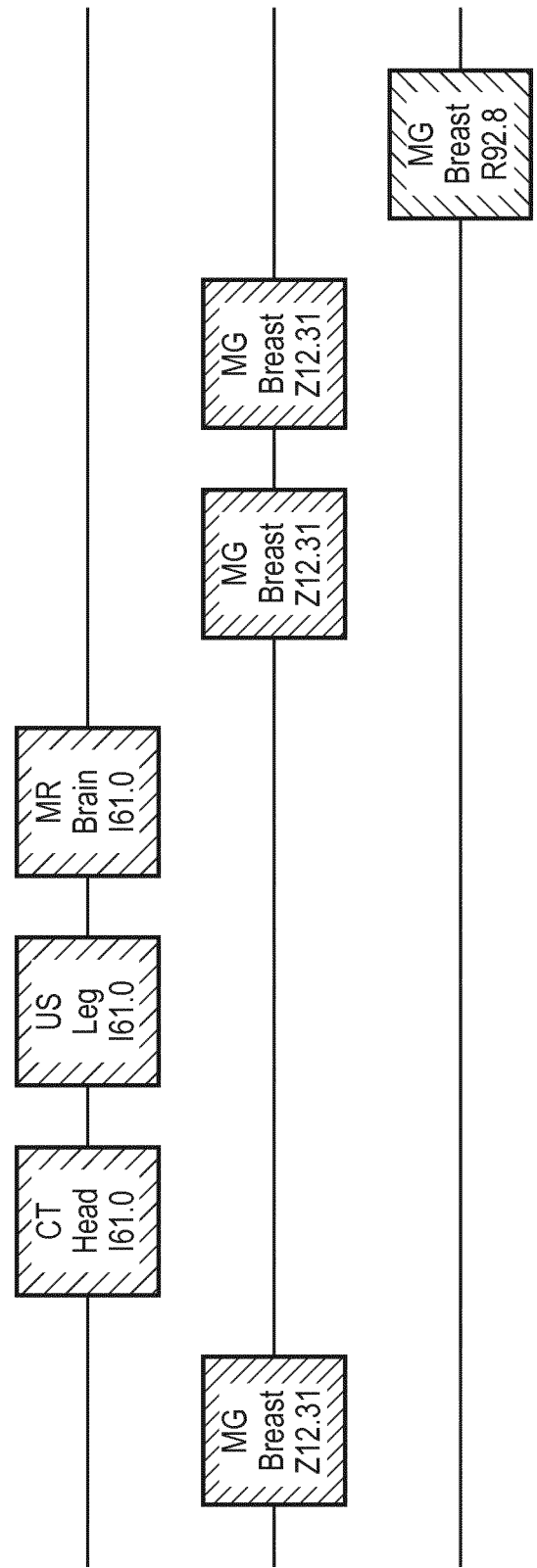
FIG. 2
FIG. 3

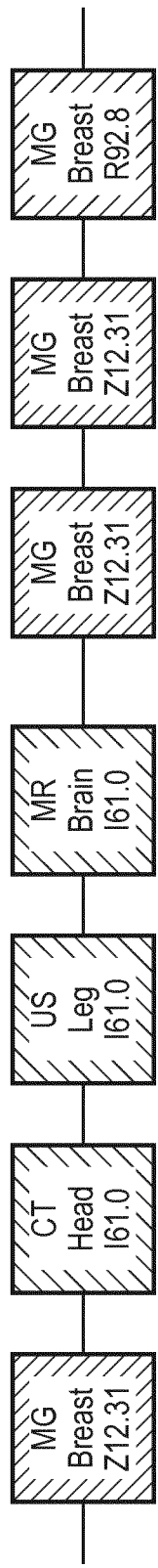
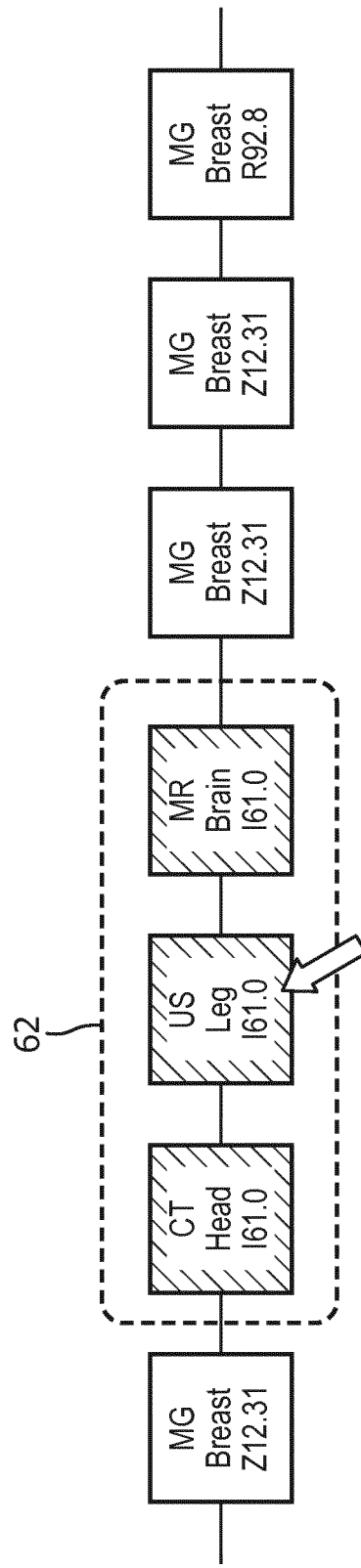
FIG. 4
FIG. 5

INTELLIGENT ORGANIZATION OF MEDICAL STUDY TIMELINE BY ORDER CODES

CROSS REFERENCE TO RELATED APPLICATIONS

This application is the U.S. National Phase application under 35 U.S.C. § 371 of International Application No. PCT/EP2018/059734 filed Apr. 17, 2018, published as WO 2018/192906 on Oct. 25, 2018, which claims the benefit of U.S. Provisional Patent Application No. 62/486,486 filed Apr. 18, 2017. These applications are hereby incorporated by reference herein.

FIELD

The following relates generally to the radiology arts, radiology report viewer arts, radiology reading arts, and related arts.

BACKGROUND

Radiologists perform readings of radiology examinations on a tight schedule. In each reading, the radiologist is expected to consider any relevant prior radiology imaging examinations that the patient may have undergone. The prior examinations are stored in an electronic chart, for example embodied as a Picture Archiving and Communication System (PACS) for general radiology images, and/or in a more specialized database such as a Cardiovascular Information System (CVIS). A radiology workstation typically provides access to these prior radiology examinations, indexed as a listing with each prior radiology examination labeled by anatomy and imaging modality. This limited amount of information may not be sufficient for a radiologist reviewing a current radiology examination to efficiently and accurately identify the past examination(s) that are relevant and should be reviewed. The radiologist may waste time clicking various past examinations and reviewing reports only to determine that those examinations are not relevant to the current examination; or alternatively, the radiologist may fail to click on a relevant past examination and may thereby miss information that would have been useful in reading the current examination.

The following discloses certain improvements.

SUMMARY

In one disclosed aspect, a radiology viewer comprises an electronic processor, at least one display, at least one user input device, and a non-transitory storage medium storing: retrieval instructions readable and executable by the electronic processor to retrieve an index of prior radiology examinations from an electronic patient chart in which the prior radiology examinations are indexed by at least date, imaging modality, and anatomical region and to retrieve billable order codes for the prior radiology examinations from an order management system, organizing instructions readable and executable by the electronic processor to organize the prior radiology examinations into groups using features of the prior radiology examinations including features comprising or generated from the billable order codes for the prior radiology examinations, and viewer instructions readable and executable by the electronic processor to display an organized index of the prior radiology examinations on the at least one display in which the prior radiology examinations are organized into the groups.

In another disclosed aspect, a non-transitory storage medium stores: retrieval instructions readable and executable by an electronic processor to retrieve an index of prior radiology examinations from an electronic patient chart in which the prior radiology examinations are indexed by at least date, imaging modality, and anatomical region and to retrieve ICD order codes for the prior radiology examinations from an order management system wherein the ICD order codes conform to an International Classification of Diseases (ICD) system; organizing instructions readable and executable by the electronic processor to organize the prior radiology examinations into groups using features of the prior radiology examinations including features comprising or generated from the ICD order codes for the prior radiology examinations; and viewer instructions readable and executable by the electronic processor to cause a display to present an organized index of the prior radiology examinations on a display in which the prior radiology examinations are organized into the groups.

In another disclosed aspect, a radiology viewing method is disclosed. An index of prior radiology examinations is retrieved from an electronic patient chart in which the prior radiology examinations are indexed by at least date, imaging modality, and anatomical region. Billable order codes for the prior radiology examinations are retrieved from an order management system. The billable order codes conform to a billable order classification system. Using an electronic processor, the prior radiology examinations are organized into groups using features of the prior radiology examinations including features comprising or generated from the billable order codes for the prior radiology examinations. On at least one display, an organized index of the prior radiology examinations is displayed in which the prior radiology examinations are organized into the groups. A selection of a prior radiology examination to be reviewed is received via a user input device interacting with the presented organized index of radiology examinations. On the at least one display, content of the radiology examination to be reviewed is displayed.

One advantage resides in providing a radiology workstation with more efficient retrieval of past radiology examinations.

Another advantage resides in providing a radiology workstation that more effectively displays information on past radiology examinations.

Another advantage resides in providing a radiology workstation that presents more information on past radiology examinations.

Another advantage resides in providing a radiology workstation with a user interface that facilitates user-adjustable grouping of past radiology examinations.

Another advantage resides in providing one or more of the foregoing benefits by leveraging existing mandatory order codes to provide requisite exam information.

Another advantage resides in providing one or more of the foregoing benefits with scalability to different medical institutions and/or geographical jurisdictions.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE D WINGS

The invention may take form in various components and arrangements of components, and in various steps and arrangements of steps. The drawings are only for purposes of illustrating the preferred embodiments and are not to be construed as limiting the invention.

FIG. 1 diagrammatically illustrates a radiology workstation for viewing radiology examinations stored in an electronic patient chart.

FIGS. 2-7 diagrammatically illustrate some illustrative radiology examination timeline displays suitably generated by the radiology workstation of FIG. 1.

DETAILED DESCRIPTION

As previously noted, the index of the prior radiology examinations conventionally displayed to the radiologist has limited information, usually including only the patient identification (PID); date of the imaging examination; imaging modality: computed tomography (CT), magnetic resonance imaging (MRI), positron emission tomography (PET), single photon emission computed tomography (SPECT), ultrasound (US), or so forth; and the anatomical region that was imaged: head, breast, leg, brain, or so forth. This limited information makes it difficult for the radiologist to assess relevance of a given past radiology examination, which can lead to unnecessary review of past examinations that are not relevant and/or failure to review past examinations that actually are relevant.

A possible way to address this deficiency is to mine the electronic patient chart for more information on the past radiology examinations. The electronic patient chart is a database containing patient medical data, and has various nomenclatures depending upon its scope of coverage. The electronic patient chart is commonly referred to as a Picture Archiving and Communication System (PACS) if it is limited to the radiology domain, or as a Cardiovascular Information System (CVIS) if it is limited to cardiovascular care data (including cardiac imaging examinations), or may be referred to as an Electronic Patient Chart, Electronic Medical Record (EMR), Electronic Health Record (EHR), or so forth if it contains a broader range of patient medical information. However, the data in the electronic patient chart relating to past radiology examinations is not necessarily useful for indexing those past examinations. For example, the stored radiology images are not text-based and hence are not readily amenable to extraction of concise indexing information. Metadata associated with the images may be concise, but often relates to narrow technical details, e.g. image resolution, field of view, or so forth, that are not particularly useful for indexing the prior radiology examination. A potentially useful source of indexing information is the radiology report for a past radiology examination prepared by a radiologist. However, much of the salient content of radiology reports is written in freeform natural language (e.g. English-language phrases, sentences, or paragraphs), and extraction of useful indexing information from freeform natural language content is prone to error and to large variation due to different choices of wording, different choices in terminology, different choices on which content to include in the radiology report, and the like. These variances are present between reports prepared by the same radiologist, are usually greater between reports prepared by different radiologists, and are likely to be even greater still for reports prepared at different imaging laboratories, different hospitals, or the like.

Improvements disclosed herein are premised on the insight that the order management system contains useful radiology examination indexing information in the form of billable order codes for the prior radiology examinations. This approach has numerous advantages. First, an order management system is maintained by virtually all medical facilities and providers, in order to support billing of medical tests, procedures, and the like to private medical insurance companies, governmental medical assistance programs such as Medicare in the United States, or so forth. Prompt updating of the order management system with each newly ordered procedure is thus required by practical business considerations, and often is also required by governmental regulations. The order management system usually employs rigidly standardized billable order codes in order to be compatible with complementary invoice management systems at insurance companies and government medical assistance agencies. For example, in the United States and much of Europe, the billable order codes for radiology examinations (and, more generally, for all medical procedures, tests, and the like) are stored at the order management system in conformance with an International Classification of Diseases (ICD) system, e.g. ICD-9, ICD-10, or so forth depending upon which ICD revision is currently implemented. As a consequence, in many jurisdictions, including the United States and much of Europe, every radiology examination will have one or more corresponding ICD order codes stored in the order management system, and these ICD order codes will have been assigned by the ordering physician or by clerical personnel at the time of entry of the physician's order into the order management system. Most insurance companies will not pay a claim unless it is identified by at least one ICD code, and the amount of payment is often determined by the ICD code(s). Thus, virtually every radiology examination in the electronic patient chart will have a corresponding record at the order management system, and that corresponding record will contain at least one ICD order code associated with the radiology examination. Yet a further advantage is that the ICD order codes are designed to concisely capture the purpose and nature of the corresponding medical test or procedure (here the radiology examination), and hence provide a concise and semantically meaningful description of the radiology examination which, as recognized herein, is useful for providing more informational content to the index of prior radiology examinations which is presented to the radiologist reading a current radiology examination.

With reference now to FIG. 1, a radiology workstation 10 includes at least one display 12, e.g. a color LCD display, a color plasma display, or so forth, and at least one user input device, e.g. an illustrative keyboard 14, an illustrative trackpad 16 (or a trackball, mouse, touch-sensitive overlay of the display 12, or other pointing device), a dictation microphone with associated transcription software, and/or so forth. The radiology workstation 10 may, for example, be embodied as a desktop computer or the like. The radiology workstation 10 is connected with an electronic patient chart 20 which is implemented on a server computer 22 and includes a non-transitory storage (e.g. hard disk, RAID, or so forth) storing prior radiology examinations each generally including one or more images 24 and a radiology examination report 26 that was prepared by a radiologist who read the images. The electronic patient chart 20 may be referred to as a Picture Archiving and Communication System (PACS) if its contents are is limited to the radiology domain, or may be referred to a Cardiovascular Information System (CVIS) if it is limited to cardiovascular care data, or may be referred to as an Electronic Patient Chart, Electronic Medical Record (EMR), Electronic Health Record (EHR), or so forth if it contains a broader range of patient medical information. The term "electronic patient chart" as used herein is intended to encompass any of these types of electronic patient charts and others that contain patient medical data useful for medical diagnosis, medical treatment planning and monitoring, and/or the like. Moreover, while a single electronic patient chart 20 is illustrated, it is contemplated to employ two or more different electronic patient charts, e.g. a PACS for general radiology images, a CVIS for cardiac ultrasound (US) images, and/or so forth. Similarly, there may be two or more different electronic patient charts for different medical institutions accessed by the radiology workstation 10. The server computer 22 may be embodied as a single computer, or two or more operatively interconnected computers, e.g. forming a computing cluster, a cloud computing resource, or the like.

Also of relevance to the present disclosure, the medical information technology (IT) environment includes the electronic patient chart(s) 20 which store medical data for patients, and also includes an electronic order management system 30 maintained on a separate server computer 32 (as illustrated; again this may be a single computer or a plurality of computers forming a cluster or cloud computing resource) from the server 22 which maintains the patient chart 20; or, the same server computer may maintain both the electronic patient chart(s) 20 and the order management system 30. The order management system 30 provides tracking of medical test or procedure orders, and usually either integrally includes or is operatively connected with other related medical IT components such as a hospital billing system, facilities scheduling system, and/or so forth (components not shown). The order management system 30 may be referred to by different nomenclatures depending upon the scope of coverage: for example, if the order management system 30 is limited to managing radiology examination orders, it may be referred to as a Radiology Information System (RIS). The term order management system as used herein encompasses any such information technology (IT) system that stores radiology examination orders in conjunction with ICD order codes or other billable order codes. The order management system 30 stores, for each order, relevant clerical information such as the order date, patient identification (PID), name of the ordering physician, or so forth. Additionally, the order management system 30 stores, for each order, one or more billable order codes, which in the illustrative examples conform to the International Classification of Diseases (ICD) system (e.g. ICD-9, ICD-10, ICD-10-CM, et cetera). In the United States and much of Europe, most medical insurance carriers and government assistance agencies (e.g. Medicare in the United. States) employ an ICD system as the billable order classification system, and usually require that any reimbursement claim for a medical test or procedure be accompanied by one or more ICD codes—the amount of payment on the claim is often tied to the ICD code(s), with a given code being assigned some maximum permissible reimbursement amount. As a consequence, assignment of the ICD code(s) for a given medical test or procedure (and of particular relevance here, a given radiology examination order) is usually done early on, and usually at the time the physician executes the order or at the latest when hospital clerical personnel enter the order into the order management system 30. While the illustrative embodiments assume the order management system 30 employs an ICD system as the billable order classification system, it is contemplated for some other billable order classification system to be employed, as appropriate for the particular country or jurisdiction forming the external context for the medical IT environment 20, 30.

The illustrative order management system 30 also includes an ICD system index 34, although this may alternatively be stored as a resource database of the electronic patient chart 20 and/or as a resource database stored locally at the radiology workstation 10, or as yet another alternative may be stored remotely as a web-based resource that is accessed via the Internet. More generally, this is a billable order classification system index 34. For the illustrative ICD example, each ICD code has an associated natural language description (e.g. descriptive natural language words, phrases, or sentences) that concisely summarize the medical test or procedure and/or the clinical condition being tested or treated. By way of non-limiting illustration, some typical ICD-10-CM codes and corresponding descriptions are given in Table 1. Additionally, the ICD codes ontology is hierarchical in nature, having a tree-shaped hierarchical relationship in which ICD codes have more generalized ancestors and more specialized child codes. For example, ICD codes beginning with the letter "I" relate to diseases of the circulatory system; ICD codes "I60" through "I69" relate more specifically to cerebrovascular diseases; and ICD codes of the form "I61.x" where "x" is a sub-value relate to specific types of non-traumatic intracerebral hemorrhage while ICD codes of the form "I63.x" relate to specific types of cerebral infarction, and so forth.

TABLE 1

| ICD-10-CM order code | Description |
| --- | --- |
| I61.0 | Nontraumatic intracerebral hemorrhage in hemisphere, subcortical |
| I61.1 | Nontraumatic intracerebral hemorrhage in hemisphere, cortical |
| I61.2 | Nontraumatic intracerebral hemorrhage in hemisphere, unspecified |
| R92.8 | Other abnormal and inconclusive findings on diagnostic imaging of breast |
| Z12.31 | Encounter for screening mammogram for malignant neoplasm of breast |

A radiologist employs the radiology workstation 10 to read a current radiology examination. More specifically, the images of the current examination are downloaded from the electronic patient chart 20 to the radiology workstation 10, where the radiologist can view selected images (and/or portions of images) on the display 12, and can interact with the images, e.g. by performing zoom/pan operations, using a user input device 16 to contour or otherwise define/identify/delineate image features, and/or so forth. The radiologist generates a radiology report describing the radiologist's clinical findings drawn from review of the images of the current radiology examination, e.g. typed in using the keyboard 14 and/or delivered by dictation via a dictation microphone and transcription software (features not shown). The completed radiology report is stored at the electronic patient chart 20 with the images. During the reading of a current radiology examination, it is expected that the radiologist will take into consideration any prior radiology examinations that the patient may have had in the past. These are stored in the past radiology examinations/reports database 24, 26. However, not every prior radiology examination can be expected to be relevant. Accordingly, the radiologist is initially presented with an index of the prior radiology examinations, and can select one or more of the indexed prior radiology examinations for retrieval from the electronic patient chart 20 and review at the display 12. Conventionally, the presented index of the prior radiology examinations represents each prior radiology examination by its date, the imaging modality, and the subject anatomical region. This limited amount of index information can make it difficult for the radiologist to determine which prior radiology examination(s), if any, are sufficiently relevant to justify review. The decision of which (if any) prior radiology examination(s) to review is made more difficult due to the typically tight time constraints under which a radiologist sometimes operates. For example, in some radiology settings, the radiologist may be expected to complete each examination reading in a few minutes to a few tens of minutes, depending upon the type and complexity of the radiology examination being read.

In improvements disclosed herein, this limited amount of indexing information is supplemented by additional indexing information obtained from the billable order codes (e.g. ICD order codes) stored in the order management system 30. To this end, an interactive timeline user interface (UI) 40 is executed by the server computer 22 maintaining the electronic patient chart 20. (Alternatively, part or all of the interactive timeline UI 40 may be executed at another computing device, such as at the radiology workstation 10 and/or the computer 32 maintaining the order management system 30). The interactive timeline user interface (UI) 40 operates by the electronic processor 22 executing order codes retrieval instructions 42 in which the order codes (e.g. ICD order codes) for each radiology examination are retrieved. The matching of the order in the order management system 30 with the radiology examination in the electronic patient chart 20 can be explicit, e.g. if the hospital employs a unique identifier for each test or procedure in both systems 20, 30. Alternatively, the match can be based on matching appropriate fields, e.g. the patient identifier (PID), physician name, order execution date, and laboratory identifier fields in both systems 20, 30.

By execution of organizing instructions 44 by the electronic process 22, the prior radiology examinations are organized into groups using features of the prior radiology examinations including features comprising or generated from the billable order codes for the prior radiology examinations obtained by the retrieval instructions 42. The organization may, for example, employ a simple grouping in which prior radiology examinations having the same order codes (e.g. "I61.0") are grouped together. To obtain more generalized grouping, order codes in the same family may be grouped together, e.g. all radiology examinations having order codes in the range "I60" through "I69" relating to cerebrovascular diseases may be grouped together. In addition to features comprising or generated from the billable order codes, the executing organizing instructions 44 may employ other features. For example, as illustrated in FIG. 1, concept extraction instructions 46 may be executed by the electronic processor 22 to process the radiology reports 26 of the prior radiology examinations to extract medical keywords or phrases, and conversion instructions 48 may group and/or uniformize these keywords to form standardized concepts, e.g. using a SNOMED-ICD lexicon 49 or other appropriate reference (e.g. a RadLex). These ontologies have hierarchical relationships between the medical concepts, which can be used as is or a new hierarchical relationship can be created from the one or more pre-existing relationship. If the concept extraction instructions 46 specialize at detecting concepts from one lexicon, then a mapping table such as the illustrative SNOMED-ICD lexicon 49 can be used to translate its output to another lexicon. This allows, for example, to convert SNOMED concepts to ICD codes to provide additional ICD-compliant features for organizing the radiology examinations. It is also contemplated to detect specific sections in a radiology report and to extract concepts only from certain report sections (e.g., only clinical history). The organizing instructions 44 also preferably operate to tag each prior radiology examination (or its index entry) with semantic labels representing the features used in the organizing.

By execution of viewer instructions 50, an organized index of prior radiology examinations is generated and displayed in accord with the organization output by the organizing instructions 44. Some of this processing, such as the display formatting, may be performed at the radiology workstation 10. The viewer instructions 50 display the index of prior radiology examinations on the display 12 as a timeline or other chosen format, with each prior radiology examination being represented in the timeline or other index by information typically including the imaging modality and the anatomical region imaged as is conventional, but also including further information obtained from the ICD order codes as disclosed herein. The organized index of the prior radiology examinations may be organized into the groups formed by the organizing instructions 44 by color-coding the prior radiology examinations using colors corresponding to the groups. Additionally or alternatively, the organized index of the prior radiology examinations may be organized into the groups by spatial segregation of the prior radiology examinations into display regions of the display corresponding to the groups. In the latter case, non-transitory storage medium may further store instructions readable and executable by the electronic processor 10, 22 to receive via the at least one user input device 14, 16 a drag-and-drop operation that drags a prior radiology examination to be moved from a current display region corresponding to a current group to a different display region corresponding to a different group, and to re-group the prior radiology examination to be moved from the current group to the different group in response to this drag-and-drop operation. The viewer instructions 50 are also preferably readable and executable by the electronic processor 10, 22 to receive a selection of a prior radiology examination to be reviewed via the at least one user input device 14, 16 interacting with the displayed organized index of radiology examinations. Content of the selected prior radiology examination (e.g. images and/or the written radiology report) is then displayed on the display 12 for review by the radiologist using the standard radiology examination display/review capabilities of the radiology workstation 10.

In some embodiments, the resulting organized index of prior radiology examinations may be stored in a data storage 52 to provide persistence of the organization data representing the organization of the prior radiology examinations into the groups, and further instructions readable and executable by the electronic processor 10, 22 operate to retrieve the persistence data from the non-transitory storage medium 52 and invoke the index viewer instructions 50 to display the organized index of the prior radiology examinations on the at least one display 12. This enables the output of execution of the instructions 42, 44, 46, 48 to be re-used. Alternatively, the storage 52 may be omitted, and the instructions 42, 44, 46, 48 may be re-executed to re-create the organized index each time a radiologist performs a reading of a new radiology examination for the patient.

Having provided an overview with reference to FIG. 1 of an illustrative radiology reading environment providing an index of prior radiology examinations organized (at least in part) by billable order codes of the examinations, some more specific illustrative examples are presented in the following.

For a given patient, the ICD codes retrieval instructions 42 retrieve the patient's timeline of prior radiology examinations from the PACS or other electronic medical chart 20 and the associated order codes from the RIS or other order management system 30. If the concept extraction instructions 46 are implemented, ICD-equivalent codes can also be generated from the radiology reports using a suitable lexicon 49. Since at least one ICD order code is generally required for billing purposes for each ordered radiology examination, it can be reasonably expected that each radiology examination will have at least one ICD order code associated with it. Optionally, the codes can be filtered. For instance, a code count can be computed for each ICD order code across all radiology examinations, and if an imaging study contains more than one code then the code having maximum count amongst all radiology reports is preserved and the rest are removed.

In an illustrative approach, the prior examinations organizing instructions 44 operate to group the order codes in at most N groups of codes (or "code groups") that are maximally similar within each group and maximally dissimilar between any two groups. In one implementation, the organizing instructions 44 have a threshold N that determines the maximum number of groups in which the imaging studies are partitioned. In the same or an alternate implementation, the organizing instructions 44 have another threshold M that indicates the minimum number of order codes per group. In yet another contemplated variant, the thresholds N and M are not fixed but functionally dependent on one or more contextual parameters, including but not limited to the number of prior radiology examinations, the number of unique codes, the number of unique modality and anatomies among the exams, and the weight score distribution of the different groups.

In the following, three illustrative approaches to grouping the order codes are described: (1) grouping on lexicons, i.e., ontologies with no relationship between their codes; (2) grouping on ontologies with a tree-shaped relationship between their code (ICD); and (3) grouping on ontologies with any relationship ("network") between their codes (SNOMED). Each of these illustrative examples is described in turn.

In a grouping on lexicons approach, the frequency of the order codes is counted. The first M codes each occurring at least N times are selected. In this implementation a code group consists of one single ICD order code. If the number of unique codes exceeds M, then the first M−1 codes each occurring at least N times can be selected, and one default group is created that contains the remaining, i.e., less frequent, order codes. In this grouping approach, all ICD code groups will be singletons except for maybe the one default group.

In a grouping approach that leverages a tree-shaped relationship, the term "hierarchy" is used here in reference to the tree-shaped relationship. A data structure can be used that embeds the hierarchy in which each ICD order code is endowed with a counter with default value 0. All order codes associated with the studies are mapped onto the data structure, meaning that the counter for each order code is increased with 1. In an abstraction step, for each code in the data structure with count greater than 0, the counts of all its ancestors are increased by 1. Thus, as a result, the counter of the root of the data structure equals the total number of order codes obtained from the radiology examinations. A buffer (B) of order codes is maintained representing the current set of created groups. Initially, the buffer B only contains the root code. The following algorithm splits up the groups in B by one or more groups, each being more specific than its ancestor:

While B contains ≤N concepts:
  Create another buffer B' that is empty
  For each code C in B:
    1) If C has a child that has count equal to that of C, add that child to B'. This will guarantee that the most specific ancestor is selected for a group of codes.
    2) If C has n>1 children with count ≥M, assign it a weight equal to a function of the counts of itself and its children.
    3) If C has no children, add it to B'.
  Order the codes that were assigned a weight by rule (2) from high to low; iteratively walk through the ordered list and for each code add its children that have non-zero weight if this would not cause B' to contain >N codes.
  If B equals B', return B; otherwise assign B' to B
Return B.

In rule (2) of the above algorithm, the function prioritizes the groups that are broken up. An entropy-based function can be used. For instance, if the children $D_1$, $D_2$, and $D_3$ of a code C have counts 10, 5 and 1, respectively, then the entropy can be computed for the corresponding stochastic variable that has likelihoods 10/16, 5/16 and 1/16 for each of the three values it can assume, 16 being the sum of the counts of the children: 10+5+1. Entropy may be defined as follows:

$$H[C] = -1 \times (\Sigma_{D_i} P(D_i) \times \log_2[P(D_i)])$$

This entropy function favors splits of codes that are roughly equally likely. For instance, it will prefer to split a code whose children have counts 8 and 8 over the previous code.

In another implementation, the probability $P(D_i)$ is obtained by dividing the count of $D_i$ by the sum of the counts of the siblings' parent C. This metric will penalize splitting codes that themselves are frequent.

An alternative embodiment of rule (2) removes outliers. In this sense, it does not necessarily consider all children with count greater than or equal to M, but, in addition, requires that none of these codes are outliers according to a pre-define criterion (i.e., relative frequency greater than 1%). In this manner, if code C would have three codes $D_1$, $D_2$, and $D_3$ with respective counts 100, 100 and 1, weight is computed based on the first two as the third is considered an outlier. If this code is split, only $D_1$ and $D_2$ are added to B' and $D_3$ is added to a second buffer that contains the codes of unrelated radiology examinations.

In another implementation each ICD order code has a flag indicating if it can be split. A rule can be used that acts on this flag that has priority over the other rules:

0) If C is flagged as "do not split", add C to B'

In a variant embodiment, the "do not split" flag is functionally dependent on one or more contextual parameters, including but not limited to the number of exams, the number of unique order codes, and the number of unique modality and anatomies among the exams. In another variant embodiment, the thresholds or threshold functions are externally configurable by the radiologist and/or can be changed, e.g. using control inputs of the prior radiology examinations index viewer implemented by execution of the instructions 50 by the electronic processor 10, 22.

A grouping approach that leverages network relationships is next described as a further illustrative example. Let a distance function d be given that maps any two ICD order codes onto a distance score between 0 (maximally distant)

and 1 (maximally close). The relationship of a network can be used to determine a default function, such that:

$d(C, C')=1/(x+1)$, where x is the minimum number of steps required to walk from C to C' in the network. If C=C', then x=0 and d(C, C')=1

If the relationship in the network is asymmetric, this can be leveraged as well. For instance, the "is-a" relationship is asymmetric: C is-a C' does not generally imply C' is-a C. Thus, the distance function can be refined as follows:

$d(C, C')=1/(x+1)$, where x is the minimum number of steps along the relationship in the same direction required to walk from C to C' in the network The edges in the network may themselves be weighted. These weights can be included in the distance function as follows:

$d(C, C')=w_1 \times \ldots \times X_n$, where $w_1, \ldots, w_n$ are the weights on the edges of the shortest path in the network from C to C'. We can postulate that $d(C, C')=1$ if C=C'

If the edges are asymmetric, two weights can be associated with each edge. In one contemplated implementation, these two weights are the same, but that does not necessarily need to be the case.

The graph that is defined by the ICD order codes and the distance function (e.g., one of those presented above as illustrative examples) can be fed to a GRAPH PARTITION algorithm with parameters M and N as above. The output of a GRAPH PARTITION algorithm is a partitioning of the codes into at most M groups minimizing the distance d(C, C') between codes C and C' that sit in distinct groups. If the organization data storage 52 is implemented, the organizing instructions 44 can query it to adjust the distance weights. For instance, if one or more radiology examinations with code C were manually added to an radiology examinations group with code C', then this will increase the pre-existing distance between C and C': d(C, C')+0.1. Likewise, if a radiology examination was removed from a group, the distance can be lowered.

In the following, some illustrative embodiments and aspects of the prior examinations index viewer implemented by execution of the instructions 50 by the electronic processor 10, 22 are described. If a radiologist has previously interacted with the patient's prior examinations index timeline, the visualization this timeline can be shown and the radiology examination currently being read can be shown, not related to any exam. Using simple rules, a match can be established with the codes of any extant radiology examination groups and the ICD order code(s) of the radiology examination currently being read. Optionally, the organizing instructions 44 may be invoked to more precisely determine placement of the radiology examination currently being read in the context of the organization determined for the prior radiology examinations. On the other hand, if the radiologist has not previously interacted with the patient's organized timeline before (or if the persistence data storage 52 is not provided), then the organizing instructions 44 are invoked to generate the organization for the prior examinations index.

With reference to FIG. 2, in an illustrative timeline, prior radiology examinations are retrieved, and plotted along a time line. In FIG. 2 and the following figures, each block represents a prior radiology examination. The acronym of the top text line of each block represents the imaging modality: "MG"=mammogram or mastograph; "CT"=transmission computed tomography (CT) imaging; "US"=ultrasound imaging; and "MR"=magnetic resonance imaging (MRI). The middle text line of each block labels the anatomical region ("Breast", "Head", "Leg", "Brain", being illustrative examples). The bottom text line of each block labels the principal ICD order code associated with each radiology examination. While actual ICD codes are listed in FIGS. 2 and 3, in another embodiment these may be replaced by concise semantic descriptions corresponding to the ICD order codes taken from the billable order classification system index 34 (see FIG. 1).

With reference to FIG. 3, the prior radiology examinations of FIG. 2 may be organized into the groups generated by the organizing instructions 44 by spatial segregation of the prior radiology examinations into display regions of the display corresponding to the groups, e.g. as different "sub"-timelines in illustrative FIG. 3. Each group is associated with one or more ICD order codes not shared with any of the exams in the other groups. A multi-level timeline is depicted in FIG. 3, where each level corresponds to an ICD order code group produced by the organizing instructions 44. On each sub-timeline, all radiology examinations are positioned that have an ICD order code contained in the sub-timeline's code group. As also illustrated in FIG. 3, the prior radiology examinations may additionally be organized into the groups by color-coding the prior radiology examinations using colors corresponding to the groups (where FIG. 3 diagrammatically indicates the different colors by different types of cross-hatching).

FIG. 4 illustrates an alternative representation in which the "sub"-timelines are not used, and instead only the color coding (diagrammatically indicated by different shading types) is employed to visually organize the prior radiology examinations into the groups.

In embodiments in which the organizing instructions 44 leverage the hierarchical or tree-shaped relationship of the ICD system of the ICD order codes to organize the radiology examination into groups, each ICD order code group has one "most abstract" code, i.e. the code highest in the hierarchy (that is, closest to the "root" of the hierarchy tree). Each sub-timeline can be labelled with that most general code. Instead of the label, also icons or a color scheme can be used which is associated with the codes.

With reference to FIG. 4 and with further reference to FIG. 5, selection of a group of radiology examinations is shown. Starting with FIG. 4, a radiologist moves a mouse pointer 60 to select one group 62 of examinations, as shown in FIG. 5. In this illustrative example, the radiology examinations of the group 62 all have associated ICD order code I61.0 corresponding to the semantic description "Nontraumatic intracerebral hemorrhage in hemisphere, subcortical" (see Table 1).

The viewer user interface implemented by execution of the instructions 50 by the electronic processor 10, 22 is optionally responsive to selections by the radiologist (via a user input device 14, 16) to see more or less detail in the timeline, for instance by a slider control. If the radiologist wants to see more detail, the organizing instructions 44 can be invoked with adapted parameters M and/or N. More detail can also in some embodiments be obtained within a group of exams. This can be triggered by, for instance, double clicking a group of image exams; or by hovering over a group of exams and "zooming in" through the scroll wheel. A subdivision of a group of radiology examinations is computed by invoking the organizing instructions 44 with only the codes associated with the subset of examinations in order to generate the subdivisions.

Figure 6:
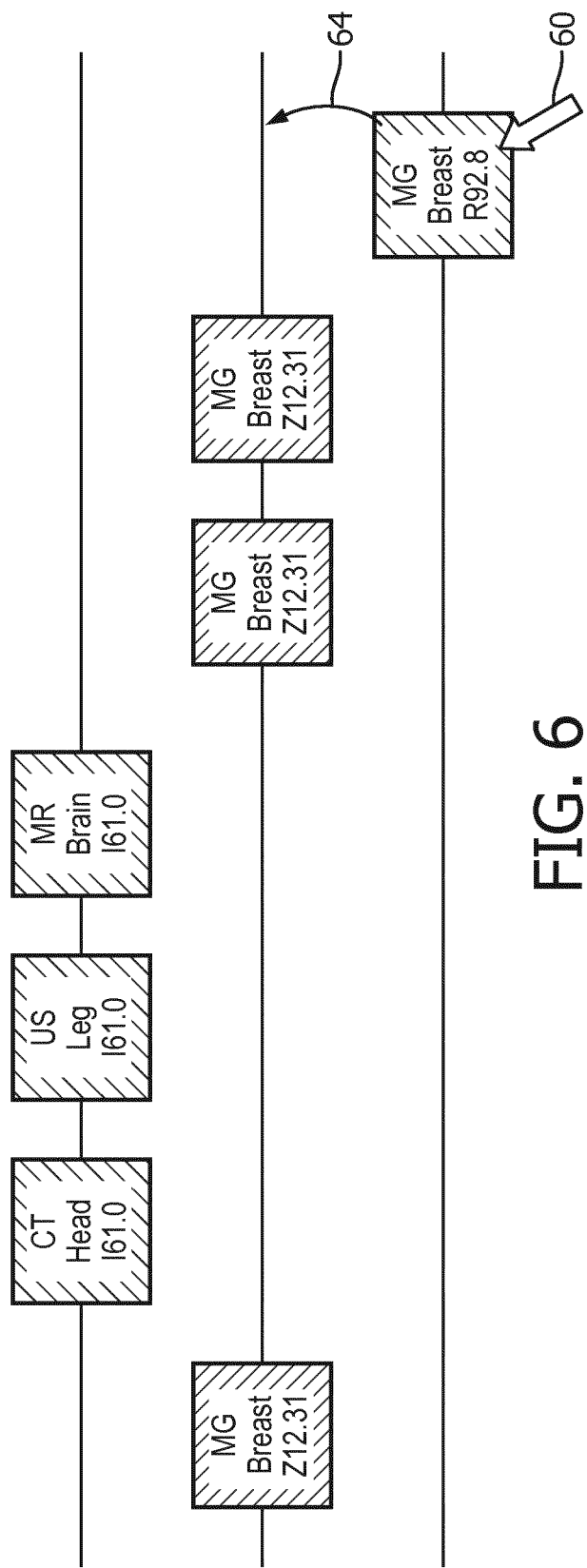
Figure 7:
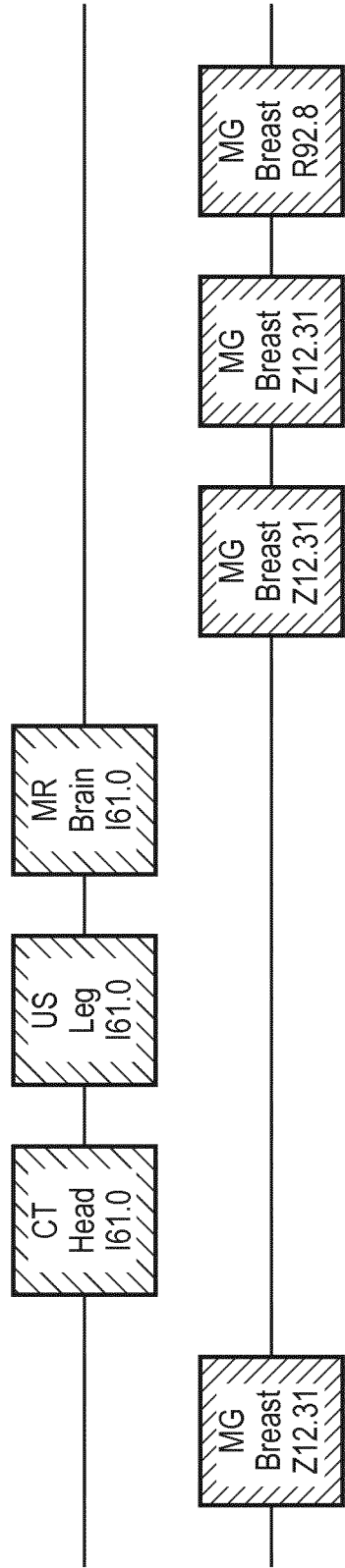

With reference to FIGS. 6 and 7, an example of merging two groups of radiology examinations is shown. In FIG. 6, the radiologist operates the mouse pointer 60 to execute a drag-and-drop operation (diagrammatically indicated by arrow 64) to drag the mammogram (MG) breast examination with ICD order code R92.8 ("Other abnormal and inconclusive findings on diagnostic imaging of breast"; see Table 1) into the group of radiology examinations which are mammogram (MG) breast examinations with ICD order code Z12.31 ("Encounter for screening mammogram for malignant neoplasm of breast"; see Table 1). FIG. 7 shows the result, in which the moved mammography breast examination with order code R92.8 is now added to (i.e. merged with) the group of mammography breast examinations with order code Z12.31. Such a merger may be desired by the radiology since all these mammography examinations are likely to be relevant to the reading of any future mammography examination. In similar fashion, drag-and-drop or other known graphical user interface (GUI) manipulations may be employed to remove an examination from a group, merge two examination groups, split an examination group, or so forth.

When the radiologist modifies the organized index of prior radiology examinations, e.g. using operations depicted in FIGS. 5-7, the updated organization is optionally stored in the persistence database 52 of FIG. 1. For instance, in the case of FIG. 6, a record can be insert to the effect that code R92.8 with frequency 1 was added to code Z12.31 with frequency 3. Contextual parameters can be added including the radiologist's profile, characteristics of the current exam, and a disease profile of the patient (e.g., the patient's problem list code). The persistence store 52 can be queried for the changes that were made previously to specific patient's prior examinations timeline. Thus, whenever a patient's timeline is being created, those changes can be incorporated, so the radiologist does not have to make them twice. In a variant embodiment, the persistence store 52 can be queried for changes that were made on all or a large subset of patients. Such information may be leveraged to generate or revise a distance function (e.g. used in grouping approaches that leverage network relationships as described previously). This functionality can also be applied if the base ontology is a lexicon, i.e., has no relationship at all, so as to create a distance function ab initio. This type of learning capability improves performance for new patients. In yet another variant embodiment, the queries are profile specific, so that the query retrieves records of users that are similar to the current user. In this manner, if a nurse makes changes to a timeline, other nurses may see those, but not, say, radiologists. Rule based logic can be employed to determine which user sees what updates.

The detailed workflow for a specific patient may depend on the previous interaction with that patient. For example, in a workflow of a user (or user with similar profile) who has interacted with timeline before, the user opens the patient chart 20 in the context of a current radiology examination being read, and patient's timeline is presented with all prior radiology examinations as configured previously (this information is obtained by reading the persistence store 52). The user associates the current study with any of the groups on the timeline.

In a workflow suitable for a user (or user with similar profile) who has not previously interacted with timeline, the user opens the patient chart 20 in the context of a current radiology examination being read, and the patient's timeline is presented with all prior radiology examinations grouped per the output of the prior examinations organizing instructions 44 (optionally as boosted by output of the concept extraction instructions 46 translated to ICD-type codes by the conversion instructions 48 using the conversion lexicon 49). The user then adapts the timeline as desired.

In a workflow suitable for a user (or user with similar profile) who retrieves a partial timeline of only relevant studies, the radiologist opens a patient chart 20 in the context of a current radiology examination being read, and the study timeline is presented as normal. The radiologist double clicks (or otherwise selects) a study on the timeline to quickly get an overview of similar studies. o After this interaction, the timeline is shows as before; no records are persisted in the persistence store 52.

It will also be appreciated that the disclosed operations of the radiology workstation 10 and related processing at the electronic patient chart 20, 22 and order management system 30, 32 may be embodied by a non-transitory storage medium, such as a hard disk drive or other magnetic storage medium, an optical disk or other optical storage medium, a solid state drive (SSD), FLASH memory, or other electronic storage medium, various combinations thereof, or so forth. Such non-transitory storage medium stores instructions readable and executable by an electronic processor (e.g. of the radiology workstation 10 and/or the server computer 22, 32) to perform the disclosed operations. For example, the instructions 42, 44, 46, 50, 52 stored on such a non-transitory storage medium are readable and executable by the electronic processor 22 (and/or by the electronic processor 10) to perform the disclosed operations.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A radiology viewer comprising:
an electronic processor;
at least one display;
at least one user input device; and
a non-transitory storage medium storing:
retrieval instructions readable and executable by the electronic processor to retrieve an index of prior radiology examinations from an electronic patient chart in which the prior radiology examinations are indexed by at least date, imaging modality, and anatomical region and to retrieve billable order codes for the prior radiology examinations from an order management system,
organizing instructions readable and executable by the electronic processor to organize the prior radiology examinations into groups using features of the prior radiology examinations including features comprising or generated from the billable order codes for the prior radiology examinations, and
viewer instructions readable and executable by the electronic processor to display an organized index of the prior radiology examinations on the at least one display in which the prior radiology examinations are organized into the groups;
wherein:
the billable order codes for the prior radiology examinations stored at the order management system conform with a billable order classification system,
the non-transitory storage medium further stores a billable order classification system index associating medical terms with the billable order codes of the billable order classification system and further defining a network of the medical terms; and
the features comprising or generated from the billable order codes for the prior radiology examinations include distances between billable order codes computed using the medical terms associated with the billable order codes retrieved from the billable order classification system index and positions of those medical terms in the network of medical terms defined by the billable order classification system index.

2. The radiology viewer of claim 1 wherein the billable order codes for the prior radiology examinations stored at the order management system conform an International Classification of Diseases (ICD) system.

3. The radiology viewer of claim 1 wherein:
the billable order codes for the prior radiology examinations stored at the order management system conform with a billable order classification system,
the non-transitory storage medium further stores a billable order classification system index associating medical terms with the billable order codes of the billable order classification system, and
the features comprising or generated from the billable order codes for the prior radiology examinations include medical terms associated with the billable order codes retrieved from the billable order classification system index.

4. The radiology viewer of claim 1 wherein:
the billable order codes for the prior radiology examinations stored at the order management system conform with a hierarchical billable order classification system,
the non-transitory storage medium further stores a billable order classification system index associating medical terms with the billable order codes of the billable order classification system and further defining a tree-structured hierarchy of the billable order classification system, and
the features comprising or generated from the billable order codes for the prior radiology examinations include features representing positions of the billable order codes in the tree-structured hierarchy of the billable order classification system.

5. The radiology viewer of claim 1 wherein the non-transitory storage medium further stores:
instructions readable and executable by the electronic processor to retrieve radiology reports of the prior radiology examinations from the electronic patient chart and to extract medical terms from the radiology reports;
wherein the features of the prior radiology examinations further include features comprising or generated from the medical terms extracted from the radiology reports of the prior radiology examinations.

6. The radiology viewer of claim 1 wherein the organized index of the prior radiology examinations is organized into the groups by color coding the prior radiology examinations using colors corresponding to the groups.

7. The radiology viewer of claim 1 wherein the organized index of the prior radiology examinations is organized into the groups by spatial segregation of the prior radiology examinations into display regions of the display corresponding to the groups.

8. The radiology viewer of claim 7 wherein the viewer instructions are further readable and executable by the electronic processor to receive via the at least one user input device a drag-and-drop operation that drags a prior radiology examination to be moved from a current display region corresponding to a current group to a different display region corresponding to a different group and to re-group the prior radiology examination to be moved from the current group to the different group.

9. The radiology viewer of claim 1 wherein the viewer instructions are further readable and executable by the electronic processor to store persistence data representing the organization of the prior radiology examinations into the groups in a persistence store.

10. A non-transitory storage medium storing:
retrieval instructions readable and executable by an electronic processor to retrieve an index of prior radiology examinations from an electronic patient chart in which the prior radiology examinations are indexed by at least date, imaging modality, and anatomical region and to retrieve ICD order codes for the prior radiology examinations from an order management system wherein the ICD order codes conform to an International Classification of Diseases (ICD) system;
organizing instructions readable and executable by the electronic processor to organize the prior radiology examinations into groups using features of the prior radiology examinations including features comprising or generated from the ICD order codes for the prior radiology examinations; and
viewer instructions readable and executable by the electronic processor to cause a display to present an organized index of the prior radiology examinations on a display in which the prior radiology examinations are organized into the groups;
wherein:
the non-transitory storage medium further stores an ICD system index associating medical terms with the ICD order codes of the ICD system and further defining a tree-structured hierarchy of the ICD system; and
the features comprising or generated from the ICD order codes for the prior radiology examinations include features representing positions of the ICD order codes in the tree structured hierarchy of the ICD system.

11. The non-transitory storage medium of claim 10 wherein:
the non-transitory storage medium further stores an ICD system index associating medical terms with the ICD order codes of the ICD system; and
the features comprising or generated from the ICD order codes for the prior radiology examinations include medical terms associated with the ICD order codes retrieved from the ICD system index.

12. The non-transitory storage medium of claim 10 wherein:
the non-transitory storage medium further stores an ICD system index associating medical terms with the ICD order codes of the ICD system and further defining a network of the medical terms; and
the features comprising or generated from the ICD order codes for the prior radiology examinations include distances between ICD order codes computed using the medical terms associated with the ICD order codes retrieved from the ICD system index and positions of those medical terms in the network of medical terms defined by the ICD system index.

13. The non-transitory storage medium of claim 10 further storing:
instructions readable and executable by the electronic processor to retrieve radiology reports of the prior radiology examinations from the electronic patient chart and to extract medical terms from the radiology reports;
wherein the features of the prior radiology examinations further include features comprising or generated from the medical terms extracted from the radiology reports of the prior radiology examinations.

14. The non-transitory storage medium of claim 10 wherein the organized index of the prior radiology examinations is organized into the groups by color coding the prior radiology examinations using colors corresponding to the groups.

15. The non-transitory storage medium of claim 10 wherein the organized index of the prior radiology examinations is organized into the groups by spatial segregation of the prior radiology examinations into display regions of the display corresponding to the groups.

16. The non-transitory storage medium of claim 15 wherein the viewer instructions are further readable and executable by the electronic processor to receive via the at least one user input device a drag-and-drop operation that drags a prior radiology examination to be moved from a current display region corresponding to a current group to a different display region corresponding to a different group and to re-group the prior radiology examination to be moved from the current group to the different group.

17. A radiology viewing method comprising:
retrieving an index of prior radiology examinations from an electronic patient chart in which the prior radiology examinations are indexed by at least date, imaging modality, and anatomical region, and to extract medical terms from radiology reports;
retrieving billable order codes for the prior radiology examinations from an order management system wherein the billable order codes conform to a billable order classification system;
using an electronic processor, organizing the prior radiology examinations into groups using features of the prior radiology examinations including features comprising or generated from the billable order codes for the prior radiology examinations, wherein the features of the prior radiology examinations further include features comprising or generated from the medical terms extracted from the radiology reports of the prior radiology examinations;
displaying, on at least one display, an organized index of the prior radiology examinations in which the prior radiology examinations are organized into the groups;
receiving a selection of a prior radiology examination to be reviewed via a user input device interacting with the displayed organized index of radiology examinations; and
displaying, on the at least one display, content of the radiology examination to be reviewed.

18. The radiology viewing method of claim 17 wherein the billable order classification system is an International Classification of Diseases (ICD) system and the billable order codes are ICD order codes.

* * * * *